United States Patent [19]

Morishita et al.

[11] Patent Number: 4,962,235
[45] Date of Patent: Oct. 9, 1990

[54] PROCESS FOR PRODUCING HIGH PURITY FORMALDEHYDE

[75] Inventors: Hirohisa Morishita; Junzo Masamoto; Tadashige Hata, all of Okayama, Japan

[73] Assignee: Asahi Kasei Kogyo Kabushiki Kaisha, Osaka, Japan

[21] Appl. No.: 333,226

[22] Filed: Apr. 5, 1989

[30] Foreign Application Priority Data

Apr. 7, 1988 [JP] Japan .................. 63-84063

[51] Int. Cl.[5] ............................. C07C 45/82
[52] U.S. Cl. .................... 568/493; 568/492
[58] Field of Search .......... 568/493, 449, 493, 449, 568/472

[56] References Cited

U.S. PATENT DOCUMENTS

| | | | |
|---|---|---|---|
| 2,678,905 | 5/1954 | Dice | 568/493 |
| 2,780,652 | 2/1957 | Gander | 568/493 |
| 2,943,701 | 7/1960 | Funck | 568/493 |
| 3,217,042 | 11/1965 | Thibault | 568/493 |
| 3,853,719 | 12/1974 | Mathias et al. | 568/493 |

FOREIGN PATENT DOCUMENTS

| | | | |
|---|---|---|---|
| 1928633 | 12/1970 | Fed. Rep. of Germany | 568/493 |
| 2359823 | 12/1975 | Fed. Rep. of Germany | 568/493 |
| 949331 | 2/1964 | United Kingdom | 568/493 |

*Primary Examiner*—Werren B. Lone
*Attorney, Agent, or Firm*—Sughrue, Mion, Zinn, Macpeak & Seas

[57] ABSTRACT

A process for producing formaldehyde having high purity is disclosed, which comprises: (A) feeding crude formaldehyde containing water and methanol to the middle or lower part of a distillation column, and feeding a polyalkylene oxide compound which is inert to formaldehyde to the upper part of the column in an amount at least 10 times the total weight of the water and methanol contained in the crude formaldehyde; (B) carrying out distillation; and (C) recovering purified formaldehyde gas from the top of the column while withdrawing a solution containing the polyalkylene oxide compound, water and methanol from the bottom of the column. Using this process, formaldehyde having stable high purity can be obtained continuously through simplified steps at low cost.

7 Claims, 1 Drawing Sheet

PROCESS FOR PRODUCING HIGH PURITY FORMALDEHYDE

FIELD OF THE INVENTION

This invention relates to a process for producing formaldehyde of high purity. More particularly, it relates to a process for producing high purity formaldehyde by extractive distillation of crude formaldehyde containing water and methanol using a polyalkylene oxide compound as a solvent. The high purity formaldehyde obtained by the invention is useful for the production of high-molecular weight polyoxymethylene.

BACKGROUND OF THE INVENTION

The vapor-liquid equilibrium of a formaldehyde-water system forms an azeotrope at a formaldehyde concentration of about 22% by weight under normal pressure. Accordingly, in general, when crude formaldehyde containing water and methanol and having a formaldehyde concentration above the azeotropic point is subjected to distillation, the formaldehyde in the liquid phase is concentrated such that paraformaldehyde, i.e., a low polymer form of formaldehyde, is ultimately precipitated. It has been therefore difficult to obtain formaldehyde having high purity by distillation of crude formaldehyde containing water and methanol.

It has been proposed to react the crude formaldehyde containing water and methanol with a higher alcohol to once form a hemiacetal, which is then dehydrated and pyrolyzed to obtain formaldehyde having a decreased water content (U.S Pat. No. 2,848,500). This technique, however, requires complicated steps and involves side reactions or denaturing. In addition, the purity of the resulting formaldehyde is unstable Hence, it has been necessary to combine this process with the purification process of a formaldehyde gas as hereinafter described before high purity formaldehyde can be obtained.

U.S. Pat. No. 2,678,905 discloses a technique for purifying a formaldehyde aqueous solution by extractive distillation. This technique aims at separating organic compounds contained in the formaldehyde aqueous solution, not water That is, the technique does not relate to the production of high purity formaldehyde by extractive distillation while avoiding azeotropy of formaldehyde with water.

Further, U.S. Pat. No. 2,780,652 discloses a process for purifying formaldehyde gas, in which formaldehyde gas having a concentration of at least 95% by weight is brought into contact with polyethylene glycol dimethyl ether in a counter-flow system. According to this process, impurities, such as water, present in 95 wt % or higher formaldehyde gas, can be absorbed in polyethylene glycol dimethyl ether to thereby obtain high purity formaldehyde gas. However, as mentioned in the patent, the process would bring no economical profit unless the starting formaldehyde has a concentration of 95 wt % or more. If the concentration is less than 95 wt %, the ratio of formaldehyde absorbed into the polyethylene glycol dimethyl ether to purify formaldehyde becomes very high.

Hence, none of the above-described conventional processes relate to the production of high purity formaldehyde directly through extractive distillation of crude formaldehyde containing water and methanol, which is produced on an industrial scale.

SUMMARY OF THE INVENTION

For the purpose of overcoming the abovedescribed problems, the present inventors have conducted extensive investigations on an industrial process for producing formaldehyde having stable high purity, which is advantageous in view of simplified steps involved and cost incurred.

As a result, it has been found in the present invention that if a polyalkylene oxide compound is added to a solution of crude formaldehyde containing water and methanol, the azeotropic composition of formaldehyde-water is shifted to the higher side of the formaldehyde concentration and, finally, the azeotropic point disappears. For instance, as shown in FIG. 1, the vapor-liquid equilibrium is shifted to the higher side of the formaldehyde concentration in the gaseous side by adding polyethylene oxide dimethyl ether to a solution of crude formaldehyde containing water and methanol. When the amount of polyethylene oxide dimethyl ether added is not less than 20 times the total weight of the crude formaldehyde composition containing water and methanol, the azeotropic composition of formaldehyde-water disappears. Thus, the disappearance of the azeotropic composition of formaldehyde-water in the vapor-liquid equilibrium means that formaldehyde and water can be separated in a good state by the distillation. In FIG. 1, the formaldehyde concentration refers to a formaldehyde concentration based on the total weight of water, methanol and formaldehyde wherein the polyalkylene oxide compound added is not contained. The present invention has been completed based on this finding It has thus been made possible to obtain highly purified formaldehyde directly from crude formaldehyde containing water and methanol by continuous distillation by adding the polyalkylene oxide compound to the distillation system in such a manner that the formaldehyde concentration in the vapor side may always be higher than that in the liquid side in a vapor-liquid equilibrium state of the formaldehyde-water system within a distillation column.

Accordingly, the present invention relates to a process for producing formaldehyde having high purity which comprises;

(A) feeding crude formaldehyde containing water and methanol to the middle or lower part of a distillation column and feeding a polyalkylene oxide compound which is inert to formaldehyde to the upper part of the column in an amount at least 10 times the total weight of the water and methanol contained in the crude formaldehyde;

(B) carrying out distillation; and (C) recovering purified formaldehyde gas from the top of the column while withdrawing a polyalkylene oxide compound solution containing water and methanol from the bottom of the column.

DETAILED DESCRIPTION OF THE INVENTION

Figure 2:
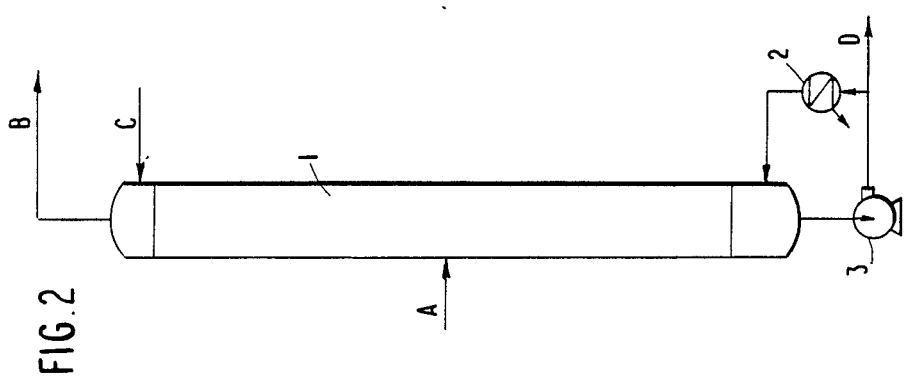
FIG. 2 is a typical system diagram for carrying out the process of the present invention.
Figure 1:
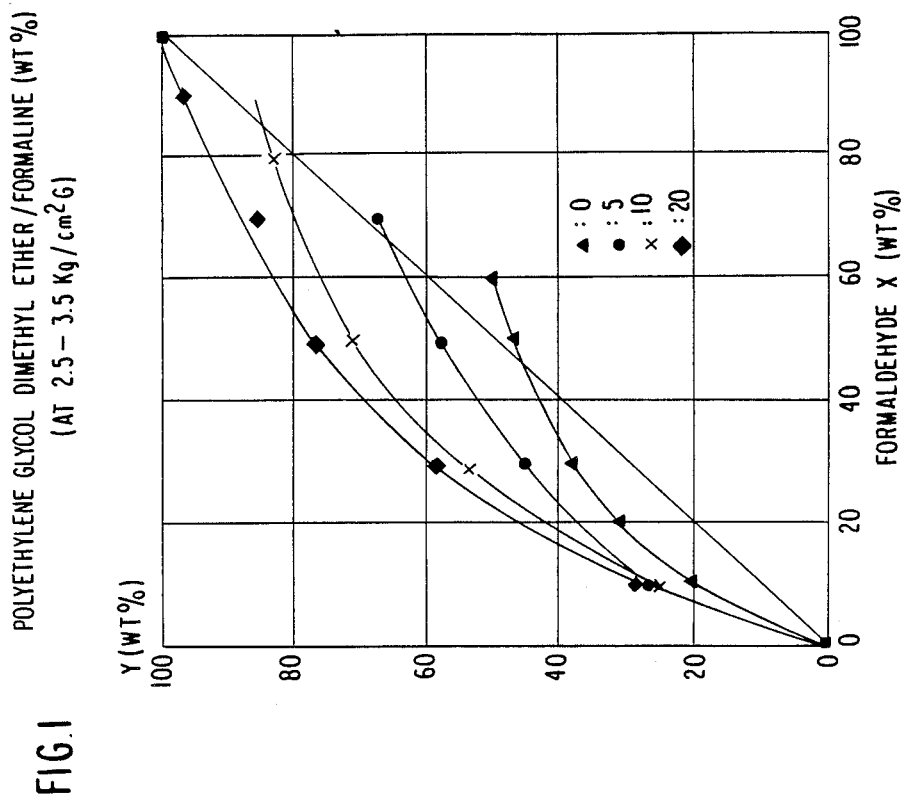
FIG. 1 is a vapor-liquid equilibrium diagram of a formaldehyde-water system when polyethylene glycol dimethyl ether having a molecular weight of 400 is added to a solution of crude formaldehyde containing water and methanol.

"Distillation" as referred to in the present invention is characterized by, unlike absorption operation, a series of operations accompanied by vaporization of a liquid in the lower part of a column and condensation of a gas in the upper portion of the column. The feature of the distillation operation according to the present invention lies in that a polyalkylene oxide compound is fed to the upper part of the distillation column and made to exist throughout the column. Therefore, the condensation of the gas in the upper part of the column is effected by the feed of the polyalkylene oxide compound to the upper portion of the column. In other words, the distillation of the present invention can be carried out by feeding crude formaldehyde containing water and methanol to the middle or lower part of the column while feeding a polyalkylene oxide compound to the upper part of the column, and vaporizing formaldehyde in the lower part of the column by heating to thereby recover purified formaldehyde.

The crude formaldehyde which is applicable to the process of the present invention comprises formaldehyde and water as main components and a small proportion, e.g., from 1 to 8% by weight, of methanol. It may also contain small proportions of other impurities, such as formic acid The formaldehyde content in the crude formaldehyde is preferably in the range of from 30 to 90% by weight, more preferably from 50 to 75% by weight If the formaldehyde content is too low, large-scaled distillation facilities is needed. If it is too high, paraformaldehyde precipitates during distillation an thus makes handling difficult.

The crude formaldehyde may be supplied in any of a liquid form, a gaseous form, and a liquid-gas mixture form.

The polyalkylene oxide compound which can be used as a solvent is a good solvent for both formaldehyde and water, which is strongly hydrophilic and serves to shift the vapor-liquid equilibrium of the formaldehyde-water system to the gaseous side of formaldehyde. It is additionally required to be inert to formaldehyde, i.e., little reactive to formaldehyde, have a boiling point higher than that of water, and be stable to both water and heat Further, it is preferred that the polyalkylene oxide compounds to be supplied to a distillation column are used in the thoroughly dehydrated forms.

Polyalkylene oxide compounds meeting such requirements include polyalkylene glycols having ethylene oxide or methylene oxide as a constituting unit and derivatives thereof, with at least 90% of their terminal hydroxyl groups being blocked with terminal groups stable to both water and formaldehyde, such as an alkylether group having from 1 to 18 carbon atoms in the alkyl moiety, an aryl ether group, a substituted alkyl ether group, and a substituted aryl ether group, wherein the term "substituted alkyl" or "substituted aryl" means an alkyl or aryl group whose hydrogen atoms are partly substituted with an alkyl or aryl group having up to 18 carbon atoms.

Specific examples of the polyalkylene glycols are diethylene glycol, triethylene glycol, tetraethylene glycol, polyethylene glycol having 5 or more ethylene oxide units, polymethylene glycol, and polytetramethylene glycol. Specific examples of the polyalkylene glycol derivatives are block copolymers comprising oxyethylene and oxypropylene or oxytetraethylene, and polyethylene glycol derivatives prepared by polymerizing ethylene oxide using a polyhydric alcohol (e.g., glycerin, pentaerythriol, sorbitol, trimethylolpropane) as a chain transfer agent.

The vapor pressure of the polyalkylene oxide compound in the distillation system is preferably as small as possible because the polyalkylene oxide compound is liable to scatter and accompany the purified gas if it has a high vapor pressure. Accordingly, a preferred vapor pressure of the polyalkylene oxide compound is 500 mmHg or less, more preferably between 0.01 and 100 mmHg, at 100° C. The higher the molecular weight of the polyalkylene oxide compound, the better from the standpoint of vapor pressure. On the other hand, a polyalkylene oxide compound having too a high molecular weight has a high melting point, thus making handling difficult.

Form all these considerations, polyalkylene oxide compounds particularly preferred in the present invention are polyethylene oxide compounds. From the standpoint of availability and cost, more preferred of them are diethylene glycol dimethyl ether, triethylene glycol dimethyl ether, tetraethylene glycol dimethyl ether, and other polyethylene glycol dimethyl ethers having at least 5, particularly from 5 to 50, ethylene oxide units, as well as the corresponding diethyl ethers. The most suitable are polyethylene glycol dimethyl ethers having a number average molecular weight of from 200 to 2,000, preferably from 200 to 1,000, more preferably from 300 to 700.

The amount of the polyalkylene oxide compound to be fed should be such that the gaseous formaldehyde concentration is higher than the liquid formaldehyde concentration in the vapor-liquid equilibrium state of the formaldehyde-water system in the distillation system, and it depends on the formaldehyde concentraion of the starting crude formaldehyde containing water and methanol and the kind of the polyalkylene oxide compound supplied. Such an amount is at least 10 times, preferably from 30 to 500 times, more preferably from 40 to 120 times, the total weight of water and methanol present in the crude formaldehyde fed. If the amount is too high, a large-scaled distillation apparatus would be required, resulting in bed economy.

Distillation conditions vary depending on the composition of the crude formaldehyde to be purified, the composition of the purified formaldehyde recovered from the top of the column, and the concentration of formaldehyde contained in the polyalkylene oxide compound withdrawn from the bottom of the column, and can be determined from the vapor-liquid equilibrium relationship of the formaldehyde-water system in the presence of the polyalkylene oxide compound and the solubility of the crude formaldehyde in the polyalkylene oxide compound.

The height of the distillation column and the stage where the crude formaldehyde is to be supplied can be decided from a stage efficiency experimentally obtained from the vapor-liquid equilibrium relationship. The height of the column portion above the stage where the crude formaldehyde is supplied must be increased as the concentration of the crude formaldehyde decreases. Further, in order to increase the recovery of formaldehyde, it is necessary to increase the height of the column portion below the stage where the crude formaldehyde is supplied Hence, the position of feeding the crude formaldehyde cannot be generally decided, but is desirably between the middle portion and just above the bottom. The position of feeding the polyalkylene oxide compound is preferably the top of the column in cases where the polyalkylene oxide compound has a small vapor pressure, i.e., 50 mmHg or less at 100° C. In cases where the polyalkylene oxide vapor pressure is relatively high, i.e., more than 50 mmHg at 100° C., some height is required above the position of feeding the polyalkylene oxide compound for recovering the polyalkylene oxide compound.

The distillation temperature preferably ranges from 80° to 200° C., more preferably 120° to 180° C. If it is less than 80° C., paraformaldehyde precipitates as formaldehyde is concentrated in the distillation system, causing various troubles on carrying out the process on an industrial scale. If it is higher than 200° C., the distillation efficiency is deteriorated, involving deterioration of the solvent.

The pressure in the distillation system preferably ranges from normal pressure to 5 kg/cm$^2$G, more preferably 1 kg/cm$^2$G to 3 kg/cm$^2$G. The distillation efficiency is deteriorated under a lower pressure, and the required operation temperature becomes high under a higher pressure.

The polyalkylene oxide compound having been used for distillation contains water, formaldehyde and other impurities and can be regenerated for recycling. Various methods of regeneration are possible, and a stripping method using an inert gas such as nitrogen under normal pressure or reduced pressure is preferred.

In order to obtain a further increased purity of the formaldehyde recovered, the process of the present invention may be combined with conventionally known purification techniques, such as washing and adsorption.

A preferred and typical flow of the process of this invention is shown in FIG. 2. In FIG. 2, crude formaldehyde containing water and methanol is fed to the middle part of distillation tower (1) from line A, and a dehydrated polyalkylene oxide compound is fed to the upper part from line C. At the bottom part of the column, the bottom liquid is made to circulate through boiler (2) by means of pump (3) to thereby boil lowboiling materials. Highly purified formaldehyde gas is recovered from the top of the column through line B. The polyalkylene oxide compound containing formaldehyde, water and other impurities at the bottom is withdrawn from line D by means of pump 3 and, after regenerated by dehydration, returned to the distillation system through line C.

The present invention is now illustrated in greater detail by way of the following Examples and Comparative Examples, but it should be understood that the present invention is not deemed to be limited thereto. In these examples, all of the percents are by weight unless otherwise indicated.

EXAMPLE 1

A distillation column of 3 inch in inner diameter and 2.5 m in height packed with a Dickson packing having a diameter of 3 mm was used. A crude formaldehyde solution consisting of 65% of formaldehyde, 32% of water, and 3% of methanol was fed to the column at a position 1.5 m below the top of the column at a rate of 300 g/hr, and polyethylene glycol dimethyl ether having a number average molecular weight of 400 (water content: 10 ppm) was fed to the top of the column at a rate of 10 kg/hr. The temperature of the fed polyethylene glycol dimethyl ether was controlled at 100° C. The pressure at the top was maintained at normal pressure and the bottom temperature was controlled at 170° C. by heating and circulating the bottom liquid.

The gas recovered from the top of the column comprised 99.87% of formaldehyde, 0.12% of water, and 0.01% of methanol; and the hydrophilic solvent withdrawn from the bottom contained 0.96% of water, 0.23% of formaldehyde, and 0.09% of methanol.

EXAMPLE 2

A distillation column of 3 inch in inner diameter and 4.5 m in height packed with a Dickson packing of 6 mm in diameter was used. A crude formaldehyde solution comprising 65% of formaldehyde, 32% of water, and 3% of methanol was fed to the column at a position 1.5 m above the bottom at a rate of 1,000 g/hr, and thoroughly dehydrated polyethylene glycol dimethyl ether (water content: 5 ppm) was fed to the top at a rate of 20 kg/hr.

The temperature of the fed polyethylene glycol dimethyl ether was controlled at 120° C. The bottom liquid was heated and circulated so as to control the pressure at the top and the temperature at the bottom at 2.0 kg/cm$^2$G and 170° C., respectively.

The bottom was continuously withdrawn and fed to the top of a column of 3 inch in inner diameter and 2.5 m in height packed with a Dickson packing of 6 mm in diameter, while supplying nitrogen gas to the lower part of the column, with the temperature in the column being controlled at 170° C., to thereby dehydrate the polyethylene glycol dimethyl ether for reuse.

The top gas recovered from the distillation column comprised 99.98% of formaldehyde, 0.015% of water, and 0.005% of methanol; and the polyalkylene oxide compound solution withdrawn from the bottom contained 1.60% of water, 0.53% of formaldehyde, and 0.15% of methanol.

EXAMPLES 3 TO 10

The same crude formaldehyde solution as used in Example 1 was fed to the same distillation column as used in Example 1 in the same manner as in Example 1. Each of the polyalkylene oxide compounds shown in Table 1 below having been thoroughly dehydrated was fed to the column from the top at a rate of 12 kg/hr.

The temperature of the fed polyalkylene oxide compound was controlled at 120° C., and the bottom liquid was heated and circulated so as to set the pressure at the top and the temperature of the bottom at 1.5 kg/cm$^2$G and 175° C., respectively.

The composition of the top gas recovered is shown in Table 1.

TABLE 1

| | Polyalkylene Oxide Compound | | Top Gas Composition | | |
|---|---|---|---|---|---|
| Ex. No. | Kind | Water Content (ppm) | Formaldehyde (wt %) | Water (wt %) | Methanol (wt %) |
| 3 | Diethylene glycol diethyl ether | 4 | 99.82 | 0.17 | 0.01 |
| 4 | Triethylene glycol | 4 | 99.90 | 0.09 | 0.006 |

TABLE 1-continued

| Ex. No. | Polyalkylene Oxide Compound Kind | Water Content (ppm) | Top Gas Composition Formaldehyde (wt %) | Water (wt %) | Methanol (wt %) |
|---|---|---|---|---|---|
| 5 | Tetraethylene glycol dimethyl ether | 3 | 99.98 | 0.02 | 0.002 |
| 6 | Polyethylene glycol dimethyl ether (Mn = 540) | 1 | 99.99 | 0.01 | 0.002 |
| 7 | Polyethylene glycol monomethylmonoethyl ether (Mn = 540) | 1 | 99.98 | 0.02 | 0.003 |
| 8 | $C_8H_{17}$—⟨⟩—$O(CH_2CH_2O)_{100}CH_3$ | 1 | 99.53 | 0.43 | 0.04 |
| 9 | Trimethylolpropane ethylene oxide adduct terminated by methyl etherification (Mn = 700) | 1 | 99.68 | 0.38 | 0.04 |
| 10 | $CH_3O(CH_2CH_2O)_n(CH_2\overset{CH_3}{\underset{|}{C}HO})_m$—$CH_3$ (n = 10; m = 2) | 1 | 99.32 | 0.63 | 0.05 |

EXAMPLE 11

Crude formaldehyde was subjected to extractive distillation in the same manner as in Example 2, except that the crude formaldehyde containing water and methanol was fed in a gasified state.

The resulting top gas comprised 99.93% of formaldehyde, 0.065% of water, and 0.005% of methanol.

EXAMPLES 12 TO 15 AND COMPARATIVE EXAMPLES 1 AND 2

The same apparatus as used in Example 1 was used, and polyethylene glycol dimethyl ether having a number average molecular weight of 400 and a water content of 5 ppm or less was fed from the top as a hydrophilic solvent. Distillation was carried out under conditions shown in Table 2.

The results obtained are also shown in Table 2.

From the results shown in Table 2, it can be seen that when the amount of the polyalkylene oxide compound fed is small as in Comparative Examples 1 and 2, the formaldehyde concentration of the top gas recovered from the distillation column is lower than those of the Examples, whereby in Comparative Examples 1 and 2, thus making the purification difficult.

TABLE 2

| Ex. No. | Crude Formaldehyde Composition Formaldehyde (wt %) | Water (wt %) | Methanol (wt %) | Crude Formaldehyde Composition Feed Rate (g/hr) | Polyalkylene Oxide Compound Feed Rate (kg/hr) | Temp. of Polyalkylene Oxide Compound Fed (°C.) | Pressure at Top of Column (kg/cm²G) |
|---|---|---|---|---|---|---|---|
| 12 | 58.5 | 39.2 | 2.3 | 300 | 15 | 110 | normal pressure |
| 13 | 70.3 | 27.7 | 2.0 | 300 | 15 | 110 | normal pressure |
| 14 | 70.3 | 27.7 | 2.0 | 300 | 5 | 90 | normal pressure |
| 15 | 70.3 | 27.7 | 2.0 | 300 | 20 | 100 | normal pressure |
| Compa. Ex. 1 | 58.5 | 39.2 | 2.3 | 500 | 1.5 | 110 | normal pressure |
| Compa. Ex. 2 | 70.3 | 27.7 | 2.0 | 500 | 1.0 | 90 | normal pressure |

| Ex. No. | Temp. of Column Bottom (°C.) | Water Content of Hydrophilic Solvent (ppm) | Top gas Composition Formaldehyde (wt %) | Water (wt %) | Methanol (wt %) |
|---|---|---|---|---|---|
| 12 | 165 | ≦5 | 99.82 | 0.17 | 0.01 |
| 13 | 170 | ≦5 | 99.98 | 0.02 | 0.005 |
| 14 | 165 | ≦5 | 99.85 | 0.13 | 0.02 |
| 15 | 175 | ≦5 | 99.98 | 0.015 | 0.005 |
| Compa. Ex. 1 | 165 | ≦5 | 64.7 | 33.6 | 1.7 |
| Compa. | 165 | ≦5 | 77.1 | 21.3 | 1.6 |

While the invention has been described in detail and with reference to specific embodiments thereof, it will be apparent to one skilled in the art that various changes and modifications can be made therein without departing from the spirit and scope thereof.

What is claimed is:

1. A process for producing formaldehyde having high purity which comprises:
   (A) feeding crude formaldehyde containing water and methanol to the middle or lower part of a distillation column, and feeding a polyalkylene oxide compound which is inert to formaldehyde to the upper part of the column in an amount at least 10 times the total weight of the water and methanol contained in the crude formaldehyde;
   (B) carrying out distillation at a temperature of from 80° to 200° C. and at a pressure of from atmospheric pressure to 5 kg/cm$^2$G and;
   (C) recovering purified formaldehyde gas from the top of the column while withdrawing a solution containing the polyalkylene oxide compound, water and methanol from the bottom of the column, wherein said polyalkylene oxide compound is a polyalkylene glycol having ethylene oxide or methylene oxide as a constituting unit with at least 90% of the terminal hydroxyl groups thereof being blocked with terminal groups stable to both water and formaldehyde.

2. The process as claimed in claim 1, wherein said crude formaldehyde has a formaldehyde concentration of from 30 to 90 % by weight.

3. The process as claimed in claim 2, wherein said crude formaldehyde has a formaldehyde concentration of from 50 to 75% by weight.

4. The process as claimed in claim 1, wherein said polyalkylene oxide compound is compound with at least 90% of its terminal hydroxyl groups being blocked with any of an alkyl ether group, an aryl ether group, a substituted alkyl ether group, and a substituted aryl ether group.

5. The process as claimed in claim 1, wherein said polyalkylene oxide compound is selected from diethylene glycol dimethyl ether, triethylene glycol dimethyl ether, tetraethylene glycol dimethyl ether, polyethylene glycol dimethyl ether having from 5 to 50 ethylene oxide units, the corresponding diethyl ethers of these compounds, and a mixture thereof.

6. The process as claimed in claim 1, wherein said polyalkylene oxide compound is polyethylene glycol dimethyl ether having a number average molecular weight of from 200 to 2,000.

7. The process as claimed in claim 1, wherein said polyalkylene oxide compound is fed in an amount of from 40 to 120 times the total weight of water and methanol contained in the crude formaldehyde fed.

* * * * *